United States Patent [19]

Erickson et al.

[11] Patent Number: 5,269,747
[45] Date of Patent: * Dec. 14, 1993

[54] DOUBLE-TRANSDUCER SYSTEM FOR PEMF THERAPY

[75] Inventors: John H. Erickson, Plano; John C. Tepper, Carrollton, both of Tex.

[73] Assignee: American Medical Electronics, Inc., Dallas, Tex.

[ * ] Notice: The portion of the term of this patent subsequent to Jan. 26, 2010 has been disclaimed.

[21] Appl. No.: 962,251

[22] Filed: Oct. 16, 1992

Related U.S. Application Data

[63] Continuation of Ser. No. 586,505, Sep. 21, 1990, Pat. No. 5,181,902.

[51] Int. Cl.$^5$ .............................................. A61N 1/00
[52] U.S. Cl. ......................................... 600/14; 600/15
[58] Field of Search ................................. 600/9-15; 128/419 F

[56] References Cited

U.S. PATENT DOCUMENTS

| | | | |
|---|---|---|---|
| 4,548,208 | 10/1985 | Neimi | 128/419 F |
| 4,654,574 | 3/1987 | Thaler | 320/12 |
| 4,850,959 | 7/1989 | Findl | 600/14 |
| 5,045,050 | 9/1991 | Liboff et al. | 600/9 |
| 5,106,361 | 4/1992 | Liboff et al. | 600/13 |
| 5,181,902 | 1/1993 | Erickson et al. | 600/15 |

Primary Examiner—Lee S. Cohen
Assistant Examiner—John P. Lacyk
Attorney, Agent, or Firm—Baker & Botts, L.L.P.

[57] ABSTRACT

A PEMF double-transducer system (FIG. 1) used for PEMF therapy (such as after spinal fusion) uses a two-transducer configuration for generating flux-aided electromagnetic fields. The semi-rigid transducers (12, 14) are conformable, anatomically contoured and flat-wound to enhance patient comfort, and incorporated with an adjustable belt (16) to provide bracing. The belt includes compartments for a drive electronics module (22), and a rechargeable battery pack (24), making the system portable. The drive electronics (FIG. 3) includes a PEMF processor (41) that executes a PEMF program for providing pulsing current to the front and back transducers at predetermined intervals, thereby activating the electromagnetic field according to a prescribed PEMF regimen.

9 Claims, 2 Drawing Sheets

DOUBLE-TRANSDUCER SYSTEM FOR PEMF THERAPY

RELATED APPLICATIONS

This application is a continuation of application Ser. No. 07/586,505, filed Sep. 21, 1990 and entitled "DOUBLE-TRANSDUCER SYSTEM FOR PEMF THERAPY", now U.S. Pat. No. 5,181,902, issued Jan. 26, 1993.

TECHNICAL FIELD OF THE INVENTION

The invention relates generally to pulsed electromagnetic field (PEMF) therapy, and more particularly relates to a PEMF system that uses two transducers to provide PEMF therapeutic stimulation to a target area of the skeletal system (such as the spine), and a method of fabricating the system.

BACKGROUND OF THE INVENTION

Pulsed electromagnetic fields (PEMF) are low-energy, time-varying magnetic fields that are used to treat therapeutically resistant problems of the musculoskeletal system. Those problems include spinal fusion, ununited fractures, failed arthrodeses, osteonecrosis, and chronic refractory tendonitis, decubitus ulcers and ligament and tendon injuries.

The specific problem to which the invention is directed is an improved PEMF spinal stimulation system for providing PEMF therapeutic stimulation to areas of the spinal column undergoing fusion or other repair (such as treatment to salvage a failed fusion).

For spinal PEMF therapy, an electromagnetic transducer is placed on the patient's back such that pulsing the transducer produces an applied or driving field that penetrates to the spinal column. The conventional approach has been to use a single flexibly packaged transducer of wires coupled to a source of driving current. The flexible transducer is conformed to the contour of the patient's back, and strapped into place. By controlling the drive electronics, an appropriate PEMF therapy can be administered.

Current spinal PEMF systems are disadvantageous in at least two respects. To allow a patient to be ambulatory during therapy, additional bracing is usually required to prevent bending that might dislodge or stress the area undergoing treatment. Also, the single transducer configuration fails to take advantage of the flux-aiding effect of a two transducer system to maximize field uniformity.

Accordingly, a need exists for an improved PEMF system that can be used without additional bracing, and provides more uniform active field to the target area than available using a single transducer configuration.

SUMMARY OF THE INVENTION

The present invention is a PEMF double-transducer system that takes advantage of flux-aiding to achieve improved field uniformity. The semi-rigid transducers are contoured and flat-wound to enhance patient comfort while obviating the need for additional bracing.

In one aspect of the invention, the PEMF double-transducer system includes front and back transducers, both including at least a primary winding with a selected number of turns encased in a shell that is at least semi-rigid. The transducers are anatomically contoured, and are physically coupled for releasably securing the transducers on either side of a target area for PEMF therapy. Drive electronics are coupled to the primary winding of both transducers for selectively generating electromagnetic fields, thereby implementing a prescribed PEMF therapy program.

In more specific aspects of the invention, each transducer includes both primary and secondary windings, and the drive electronics includes an energy recovery circuit. The secondary windings and the energy recovery circuit are active during a deenergization cycle to recover energy to conserve battery power—the secondary windings are also used to tailor the electromagnetic field.

In an exemplary embodiment, the PEMF double-transducer system is used for spinal PEMF therapy, such as for post fusion repair. For both transducers, primary, secondary and sense windings are flat wound, permitting the shell to be formed with a substantially flat cross sectional profile. The shell is a semi-rigid formable polyurethane elastomer.

The drive electronics includes a PEMF processor that executes a PEMF program for controlling the activation of the electromagnetic fields (field strength and duty cycle). In addition to implementing the PEMF therapy program, the PEMF processor collects appropriate data in memory to enable the attending health care professional to monitor the course of the therapy.

The transducers are incorporated with a belt that permits the transducers to be placed around a patient and secured in place in front and back of the patient. The belt includes compartments for a drive electronics module and (rechargeable) battery pack.

Each transducer is fabricated as follows. Primary, secondary and sense windings of adhesive coated magnet wire are wound around a flat mandrel with an appropriate anatomical shape for the transducer. The windings are bonded by heat curing the adhesive to obtain a flat-wound flexible winding bundle. The winding bundle is placed in a mold, and encapsulated in a semi-rigid shell. A bending fixture is used to configure the transducer with the selected anatomical contour.

The technical advantages of the invention include the following. The PEMF double-transducer system includes two transducers, a Helmholtz design that is magnetic flux-aiding to optimize the electromagnetic field available for stimulating the target area, and to reduce system power consumption. The transducers are configured with an anatomical contour, and with a substantially flat cross sectional profile that provides a broad contact area, thereby enhancing patient comfort. The transducers are formable with a selected degree of rigidity, and with a selected anatomical contour and profile, providing a conformable brace without any special conforming assembly or process (such as heat). The transducers can be incorporated into a belt or other securing means to provide an integrated semi-bracing design for the PEMF device. Programmable drive electronics implement a PEMF program to control electromagnetic field activation according to a predetermined PEMF therapeutic regimen, and store and provide appropriate data for monitoring the progress of the PEMF therapy. The transducers are incorporated with a belt that includes compartments for a drive electronics module and a rechargeable battery pack to provide a integrated, portable PEMF system.

BRIEF DESCRIPTION OF THE DRAWINGS

For a more complete understanding of the invention, and for further features and advantages, reference is now made to the following Detailed Description of an exemplary embodiment of the invention, taken in conjunction with the accompanying Drawings, in which.

DETAILED DESCRIPTION OF THE INVENTION

The Detailed Description of an exemplary embodiment of the PEMF double-transducer system of the invention is organized as follows:
1. Spinal PEMF System
2. Transducer Fabrication
3. Drive Electronics Module
4. Conclusion The exemplary embodiment is a self-contained portable PEMF system for providing PEMF therapy to the spinal column, such as for fusion repair.

1. Spinal PEMF System

Figure 1:
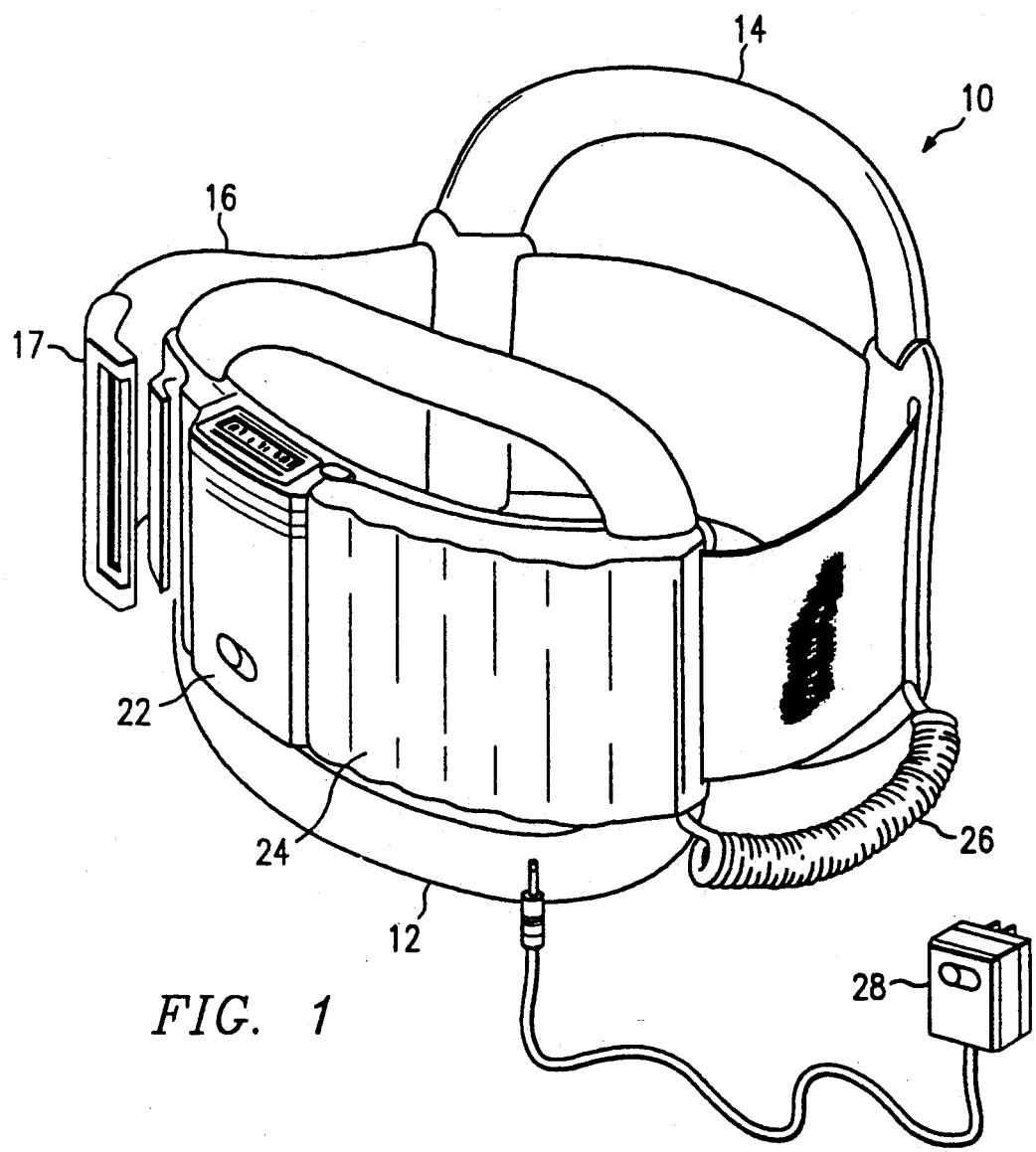
FIG. 1 illustrates an exemplary spinal PEMF double-transducer system according to the invention.

FIG. 1 illustrates an exemplary spinal PEMF double-transducer system 10. The system includes front and back transducers 12 and 14 incorporated with an adjustable belt 16.

Transducers 12 and 14 are anatomically contoured to enhance patient comfort, with a substantially flat cross sectional profile that provides a broad contact area, thereby enhancing patient comfort. The transducers are semi-rigid to maintain the selected contour and profile, and to provide bracing support as a fully integrated PEMF system. As described in Section 2, the transducers include flat-wound primary, secondary and sense windings encapsulated in a shell of a plasticized elastomer material (such as polyurethane) with a selected degree of rigidity.

The transducers include both primary and secondary windings, with the secondary windings being used to provide energy recovery, and as a collateral function, to assist in tailoring the electromagnetic field output from the transducers. Alternatively, the advantages of the PEMF double-transducer system of the invention for implementing a PEMF therapy could be obtained using a pair of transducers, each with only a primary winding (i.e., with no energy recovery windings, but preferably with an alternative efficient programmed energy format).

Adjustable belt 16 can be fastened by means of a buckle 17. The belt includes compartments for a drive electronics module 22, and a rechargeable battery pack 24.

The drive electronics module includes a PEMF processor for providing pulsing current to the front and back transducers at predetermined intervals, thereby activating the electromagnetic field according to a prescribed preprogrammed PEMF regimen. The drive electronics is coupled to the back transducer 14 by a cord 26.

The battery pack can be recharged using an AC adapter 28.

In operation, a health care professional determines a PEMF therapy that includes a regimen of PEMF stimulation of a target area of the spine. The prescribed PEMF therapy regimen is translated into a PEMF program, which is programmed into a PEMF memory in the drive electronics, either during manufacture or subsequently.

To commence a PEMF therapy session, the patient arranges the contoured front and back transducers for comfort, and engages the buckle (adjusting the belt to control snugness). Once the PEMF system is in place, the patient starts the PEMF program by turning on the drive electronics module.

In accordance with the stored PEMF therapy program, the PEMF processor correspondingly controls the activation current supplied to the transducers, thereby controlling the electromagnetic fields in terms of energization time, deenergization time and duty cycle (repetition rate). In addition to controlling the PEMF therapy, the PEMF processor maintains treatment data that is available on request to the patient (through a small display), and to a health care professional (via an I/O port) for monitoring and analysis.

2. Transducer Fabrication

For an exemplary embodiment, the front and back flat-wound contoured transducers are fabricated as follows.

Figure 2:
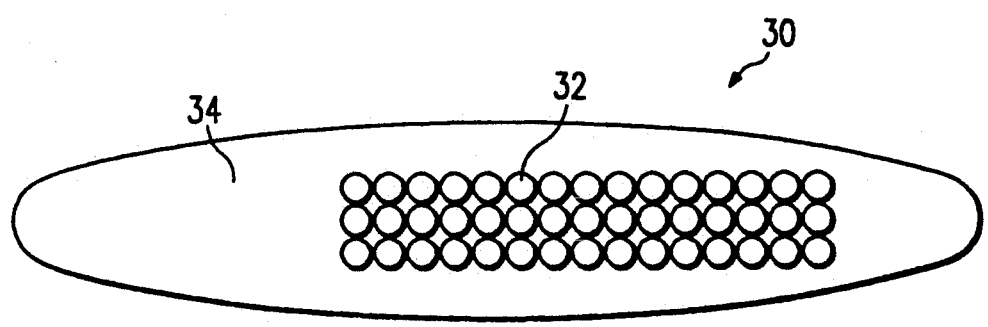
FIG. 2 is a cross sectional view of a transducer showing the flat-wound bundle of windings, and the encapsulating shell.

FIG. 2 is a cross sectional view of a transducer (front or back) 30 that includes primary, secondary and sense windings 32 encapsulated in a semi-rigid shell 34. The primary, secondary and sense windings are not shown differentiated in the figure, nor is the total number of windings shown meant to be accurate—the figure is illustrative only.

For the exemplary embodiment, a transducer includes two parallel primary windings of about 7 turns each, a secondary winding of about 35 turns, and a sense winding of at least 1 turn. For the primary and secondary windings, 18 gauge wire can be used, while 22 gauge wire can be used for the sense winding. The approximate dimensions of the winding bundle are 0.75 by 0.12 inches, while the approximate dimensions of the shell are 1.50 by 0.31 inches.

The winding material is a commercially available magnet wire that includes an overcoat of an adhesive, such as polyurethane adhesive coated wire. The shell is a polyurethane-type elastomer material, also available commercially. Other shell materials can be used to provide different degrees of transducer-shell rigidity, thereby providing different bracing rigidity characteristics.

The adhesive-coated primary, secondary and sense windings are wound simultaneously in a winding machine around a flat mandrel of the appropriate shape for the transducer. The windings are maintained in the flat-wound position shown in the figure by parallel sideplates. Once wound, the start and finish wire ends for each winding are cut to provide leads for coupling to the drive electronics, and the winding assembly—winding bundle, mandrel and sideplates—is removed from the winding machine.

The winding assembly is then placed in an oven for heat curing at the appropriate curing temperature. Heat curing activates the adhesive coating, and the windings are bonded together to form the winding bundle 32. The winding assembly is removed from the oven and, after cooling, a sideplate is removed, allowing the bonded winding bundle to be removed. The winding bundle is now in a flexible, bonded unit.

The winding bundle 32 is placed in a substantially flat mold of the appropriate shape, with the winding leads running out of the mold fill slot. The polyurethane type elastomer material is then introduced into the mold to form the shell 34.

For the exemplary embodiment, a two component polyurethane elastomer is used: an isocyanate and a polyol. In a vacuum, the two components are mixed, and then poured into the mold, covering the winding bundle. These steps are performed in a vacuum to eliminate entrapped air which can cause voids that reduce structural integrity and are cosmetically undesirable. The mold is placed in an oven for heat curing the polyurethane type elastomer material to form the encapsulating shell 34.

After cooling, the potted transducer is removed from the mold. The transducer is cleaned of mold release, and any flash is trimmed off.

Finally, the transducer is placed in a bending fixture, and bent into the desired anatomical contour. The completed semi-rigid transducer is now ready to be incorporated into the belt, and coupled to the drive electronics.

3. Drive Electronics Module

The drive electronics module includes the PEMF processor and the associated PEMF memory for storing a PEMF therapy program.

Figure 3:
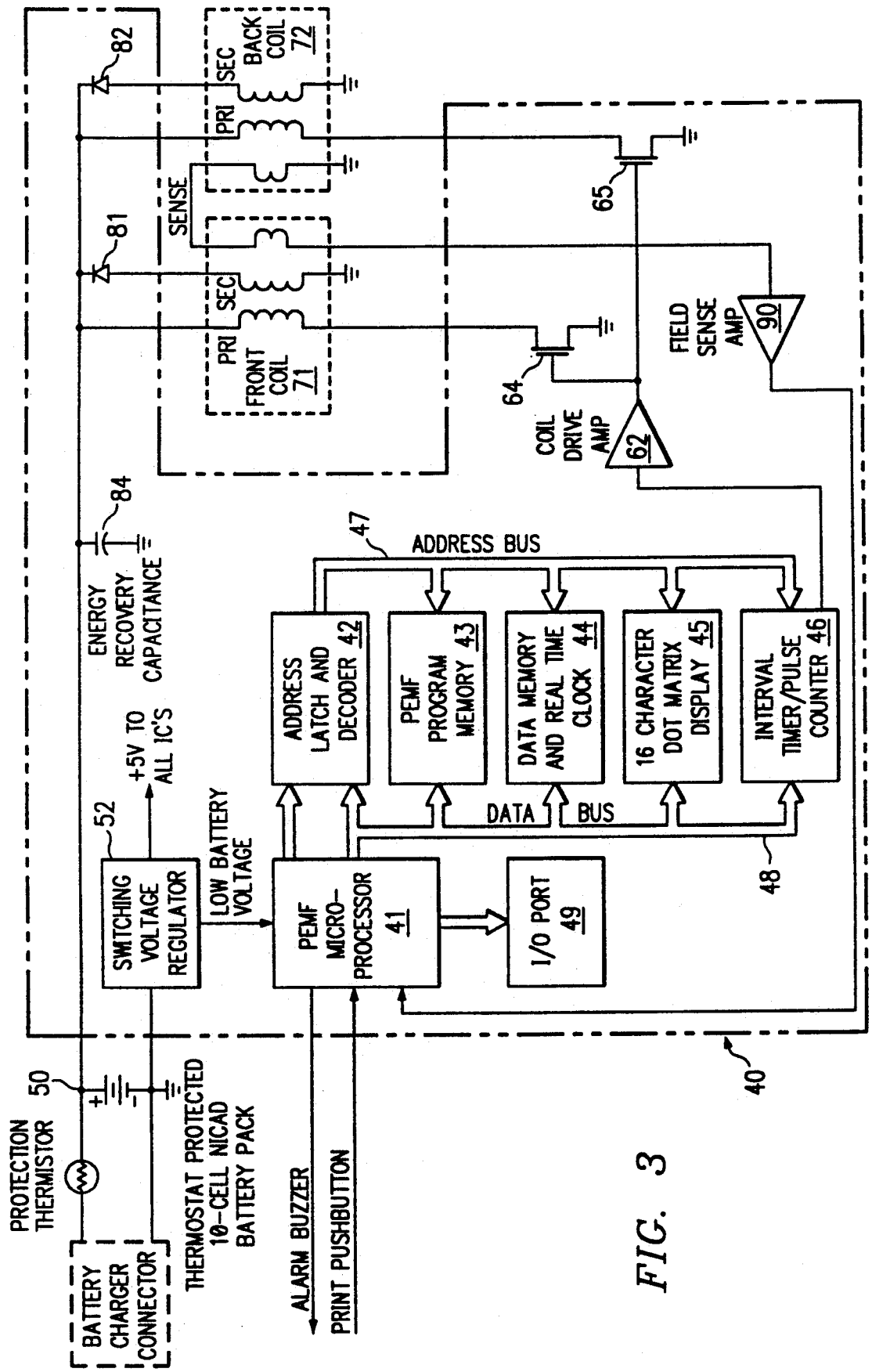
FIG. 3 is a schematic block diagram of the drive electronics.

FIG. 3 is a schematic block diagram of drive electronics 40, which includes a PEMF processor 41, with associated IC (integrated circuit) components: an address latch and decoder circuit 42, a PEMF program memory 43, a data memory and real time clock circuit 44, a 16 character dot matrix display module 45 and an interval timer/pulse counter 46. The PEMF processor is coupled to these components by an address bus 47 and a data bus 48.

A PEMF program can be loaded into an EPROM or other memory and installed as PEMF program memory 43; alternatively, the PEMF program can be read into the PEMF program memory via an I/O port 49. Data collected during execution of the programmable PEMF program parameters—such as start time, stop time, duration, and daily average —is stored in the data memory 44, and can be read out to a printer (or over a communications link) via the I/O port 49.

The PEMF processor 41 receives power from a power source, such as a 12 volt NICAD battery pack 50, through a switching voltage regulator 52 (which also provides ±5 volts power to the other IC components).

PEMF processor 41, and the supporting IC TTL logic chips and display module, function conventionally and are commercially available. For the exemplary embodiment, PEMF processor 41 is an Intel 80C51 processor. The address latch and decoder IC 42 is actually two chips, a 74HC573 and 74HC138. The PEMF program memory is a 2864 8 Kbyte EEPROM that is loaded with a PEMF program during manufacture, but that can be altered electrically while in use. The data memory and real time clock IC 44 is a Mostek MK48T02, used to store representative data about the patient's use of the PEMF system based on the internally maintained clock and calendar. The 16-character dot matrix display module 45 is a standard integrated display module package.

The interval timer/pulse counter IC 46 is an Intel 82C54 that includes two general purpose counters controlled by the PEMF processor, executing the PEMF program, to establish the duty cycle of the pulse output. The pulse output, in turn, controls the energization and deenergization of the transducers, and thereby determines the activation of the magnetic fields used in the PEMF therapy.

For the exemplary embodiment, the PEMF program causes the interval timer/pulse counter IC 46 to output a variable programmed train of, for example, 99 pulses lasting 25,740 microseconds, with a pulse period of 65 microseconds on and 195 microseconds off. That is, for each pulse, the transducers are energized for 65 microseconds and then deenergized (recovery phase) for 195 microseconds. A pulse train is output to the transducers every 667,000 microseconds (every 667 milliseconds or one third of a second).

The pulse trains from the interval timer/pulse counter 46 are input to a transducer drive amplifier 62, which control FET switches 64 and 65. The FET switches control the activation current through the primary windings of the front and back windings 71 and 72, thereby controlling the energization and deenergization of the transducers. When switched on (during a 65 microsecond on pulse), activation current from the battery 50 flows through the primary windings, energizing the transducer. When switched off (during the 195 microsecond off period), current flows through the secondary windings as the transducer is deenergized.

The other ends of the primary windings for the front and back transducers are coupled to the battery 50, as are the corresponding ends of the secondary windings through diodes 81 and 82 (the other ends of the secondary windings are grounded). A group of four energy recovery capacitors 84 release energy during transducer energization, and store energy during transducer deenergization. Thus, the energy recovery capacitors 84 and the diodes 81 and 82 for an energy recovery circuit that operates in conjunction with the secondary winding to provide energy recovery, thereby conserving battery power.

The sense winding for each of the transducers is coupled through a field sense amplifier 90 to the PEMF processor 41. The field sense amplifier senses the electromagnetic fields generated during transducer activation, and provides feedback to the PEMF processor for monitoring the PEMF operation. The PEMF processor causes appropriate monitoring data to be stored in the data memory 44, and will cause an alarm signal in the case of malfunction.

4. Conclusion

Although the invention has been described with respect to a specific, exemplary embodiment, various changes and modifications may be suggested to one skilled in the art. For example, while the exemplary embodiment is described in relation to a spinal PEMF system, the PEMF double-transducer system can be used to provide PEMF therapy for other areas of the musculoskeletal system, such as the hip or collar bone, with the transducers being being anatomically contoured positioning on either side of the target area. Also, the exemplary PEMF system is completely portable, while the advantages of the invention can be obtained from a system designed to be non-portable.

Therefore, it is intended that the invention encompass all changes and modifications that fall within the scope of the appended claims.

What is claimed is:

1. A PEMF double-transducer system for providing PEMF therapeutic stimulation to the spine of a patient's body, comprising:

front and back transducers, each including at least a primary winding with a selected number of turns encapsulated in a shell for providing support to the patient, said shells being anatomically contoured for situating on either side of a target area of the spine for PEMF therapy and physically coupled for releasably securing said transducers in place;

drive electronics coupled to said primary winding of both said front and back transducers for selectively activating an electromagnetic field, thereby implementing a prescribed PEMF therapy;

said drive electronics including a PEMF processor and a PEMF program for controlling said processor to energize and de-energize said transducers to implement a predetermined PEMF therapy program for the patient's spine;

said drive electronics also including a memory for storing treatment data including storing the patient's use of the PEMF system and the course of the PEMF therapy;

a battery pack electrically connected to said drive electronics; and a belt supporting the front and back transducers and having compartments containing the drive electronics and the battery pack, and a buckle for releasably securing the transducers in place such that PEMF double transducer system is portable.

2. The PEMF double-transducer system of claim 1, wherein:

both the front and back transducers each further include a secondary winding with a selected number of turns;

said drive electronics including an energy recovery circuit coupled to said secondary winding for recovering energy during each activation of said transducers.

3. The PEMF double-transducer system of claim 2, wherein said energy recovery circuit includes an energy recovery capacitance coupled in parallel with said primary and secondary windings.

4. The PEMF double-transducer system of claim 1, wherein both front and back transducers further include a sense winding with a selected number of sense turns, said sense winding being coupled to said drive electronics for providing a feedback indication of the PEMF output from said transducers.

5. The PEMF double-transducer system of claim 1, wherein the transducers have a substantially flat cross sectional profile.

6. The PEMF double-transducer system of claim 5, wherein:

both the front and the back transducers each further include a secondary winding with a selective number of turns; and the primary and secondary windings are flat wound.

7. The PEMF double-transducer system of claim 6, wherein the windings are adhesive coated magnet wire, bonded into a winding bundle prior to encapsulation.

8. The PEMF double-transducer system of claim 1, wherein said encapsulating shell is a polyurethane elastomer.

9. The PEMF double-transducer system of claim 1, wherein said drive electronics generates clock and calendar data, and wherein said PEMF program collects clock and calendar data representative of the patient's use of the PEMF system.

* * * * *

UNITED STATES PATENT AND TRADEMARK OFFICE
CERTIFICATE OF CORRECTION

PATENT NO. : 5,269,747
DATED : December 14, 1993
INVENTOR(S) : Erickson, et al.

It is certified that error appears in the above-identified patent and that said Letters Patent is hereby corrected as shown below:

Column 7, line 34, before "PEMF", insert -- the --.
Column 8, line 1, after "and", insert -- the --.

Signed and Sealed this

Twenty-ninth Day of November, 1994

Attest:

BRUCE LEHMAN

*Attesting Officer*  *Commissioner of Patents and Trademarks*